(12) United States Patent
Kumar

(10) Patent No.: US 6,400,316 B1
(45) Date of Patent: Jun. 4, 2002

(54) RADIATION RECEIVING APPARATUS

(75) Inventor: Balbir Kumar, Wembley (GB)

(73) Assignee: BAE Systems Electronics Limited, Farnborough (GB)

( * ) Notice: Subject to any disclaimer, the term of this patent is extended or adjusted under 35 U.S.C. 154(b) by 0 days.

(21) Appl. No.: 09/831,554

(22) PCT Filed: Nov. 12, 1999

(86) PCT No.: PCT/GB99/03783

§ 371 (c)(1),
(2), (4) Date: Aug. 13, 2001

(87) PCT Pub. No.: WO00/29837

PCT Pub. Date: May 25, 2000

(30) Foreign Application Priority Data

Nov. 12, 1998 (GB) ................................. 9824799

(51) Int. Cl.$^7$ ................................. H01Q 21/06
(52) U.S. Cl. .................. 342/362; 342/361; 359/156
(58) Field of Search ................ 342/361–366, 342/188; 359/156; 356/365

(56) References Cited

U.S. PATENT DOCUMENTS

| | | | |
|---|---|---|---|
| 2,845,622 A | * | 7/1958 | Gamble ................. 342/188 |
| 4,831,384 A | | 5/1989 | Sefton, Jr. |
| 5,507,020 A | | 4/1996 | Lee |

\* cited by examiner

*Primary Examiner*—Thomas H. Tarcza
*Assistant Examiner*—Fred H. Mull
(74) *Attorney, Agent, or Firm*—Nixon & Vanderhye P.C.

(57) ABSTRACT

A microwave receiving antenna system (30) is described which is used to determine an originating direction of microwave radiation. The system has a birefringement phase plate (34) which splits radiation incident on it into two components which undergo a differential phase delay as they pass through it. The amount of differential phase delay induced varies with angular position around the phase plate (34) from 0 at an angular position of 0° to λ an angular position of 360°. By determining the differential phase delay (assuming a previously existing relationship) the originating direction of the radiation can be determined.

25 Claims, 4 Drawing Sheets

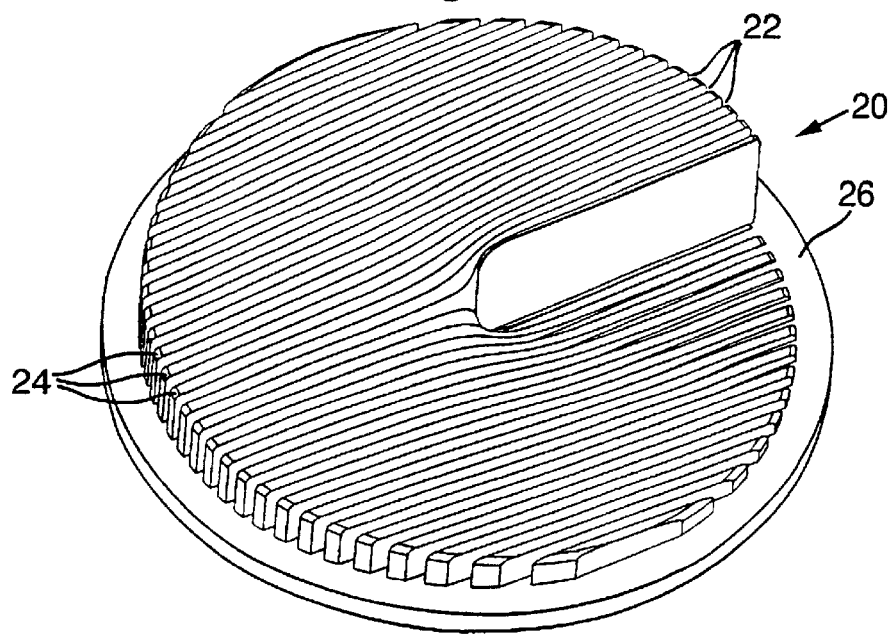
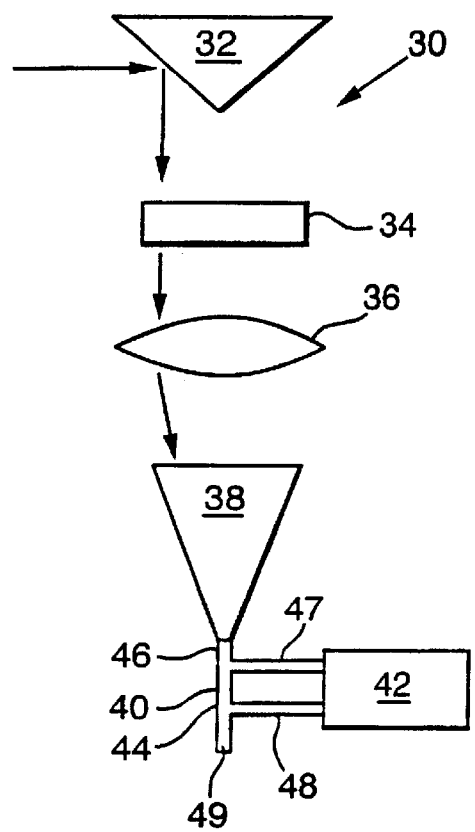

RADIATION RECEIVING APPARATUS

This invention relates to a device which is adapted to receive electromagnetic radiation. The invention is particularly, but not exclusively, concerned with systems for receiving microwave radiation.

The term microwave is generally understood to refer to the part of the electromagnetic spectrum between infra-red radiation and radiowaves. Typically this is stated to be substantially in the frequency range 1 to 300 GHz, although sometimes it is stated to be in the frequency range 0.2 to 300 GHz. It includes that part of the spectrum referred to as millimeter wave (having a frequency in the range 30 to 300 GHz).

Communications systems have been proposed in which one or more communications channels are transmitted in a particular direction in the form of a modulated electromagnetic beam propagating through free space, for example the atmosphere. An advantage of such a directional communications system over a communications system which broadcasts omnidirectionally is that there is a greater degree of security in that the communications channel or channels can be directed towards a particular location. For example, if omnidirectional transmission is used, not only can others receive the transmission readily bat the presence, and possibly the location, of the transmitting station can be determined.

In one embodiment of a communications system, units which are spatially separated need to communicate with each other. If any of the units are mobile, then the directional communications channels could come from any direction in an azimuthal plane. It then becomes important to establish the direction from which a communications channel is coming in order that a reply can be sent in the correct direction. Although this can be done by having a number of antennas pointing in different directions, a single omnidirectional antenna is preferred.

In a particular embodiment of a communications system a typical interrogation sequence might proceed as follows. The station to be interrogated is identified and an interrogating station transmits an interrogation signal. The interrogation signal typically has a first portion simply comprising a pulse of electromagnetic radiation which can be detected by the station being interrogated to know that an interrogation sequence has begun. It is not necessary for the pulse to contain any data. It may be about 100 $\mu$s long. Following the first portion, a second portion containing data is transmitted, for example in a burst 300 to 400 $\mu$s long. Therefore, the station being interrogated has 400 to 500 $\mu$s to find out the direction from which the interrogation signal is originating in order that it can send its response signal in the correct direction.

Generally, there are systems other than communications systems in which determining the direction of origin of radiation is desirable. Such systems may be tracking systems.

According to a first aspect of the invention there is provided a system for receiving radiation comprising polarisation varying means to induce an angularly dependent variation in polarisation state and detection means to measure the polarisation state of the radiation to determine the direction from which it originates.

Preferably the polarisation varying means produces a relative change between at least two components of the radiation.

In one embodiment the polarisation varying means produces a differential phase delay between the two components. This may have the effect of converting linearly polarised radiation into circularly polarised radiation and/or vice versa. In another embodiment the polarisation varying means produces a change in the relative magnitudes of the two components. This may have the effect of rotating the polarisation state of the radiation. This may particularly have the effect of rotating the polarisation of linearly polarised radiation. Both effects may be induced by the polarisation means.

Preferably the polarisation varying means comprises a phase plate which induces a variable phase delay dependent on the angular position the radiation passes through the plate. Conveniently the phase delay is induced by the phase plate having a physical thickness which varies angularly about the phase plate. Preferably the two components pass through the phase plate. Alternatively only one component passes through the phase plate with the other serving as a reference.

Preferably the phase plate has birefringent properties which cause the components to propagate differently through the plate. The components may propagate through the plate at different speeds.

Preferably the system comprises a splitter which splits the radiation into the two components. The split may occur before the radiation has had induced in it a variation in polarisation state, or after.

Preferably the system comprises a radiation collector. This may be a horn. Preferably the radiation is microwave radiation. Most preferably it is millimetric radiation. Most preferably of all it is radiation in the Ka band (26.5 to 40 GHz). Preferably the system is a receiver in a communications system. It may be part of a composite transmitter and receiver unit.

According to a second aspect of the invention there is provided a communications system comprising a radiation receiving system in accordance with the first aspect of the invention.

According to a third aspect of the invention there is provided a method of determining the direction from which radiation originates comprising the steps of inducing a variation in polarisation state of the radiation the variation being angularly dependent and measuring the polarisation state.

An embodiment of the invention will now be described by way of example only with reference to the accompanying drawings in which:

FIG. 3 shows another phase plate;

FIG. 4 shows the phase plate of FIG. 1 located in the radiation receiving apparatus;

Figure 1:
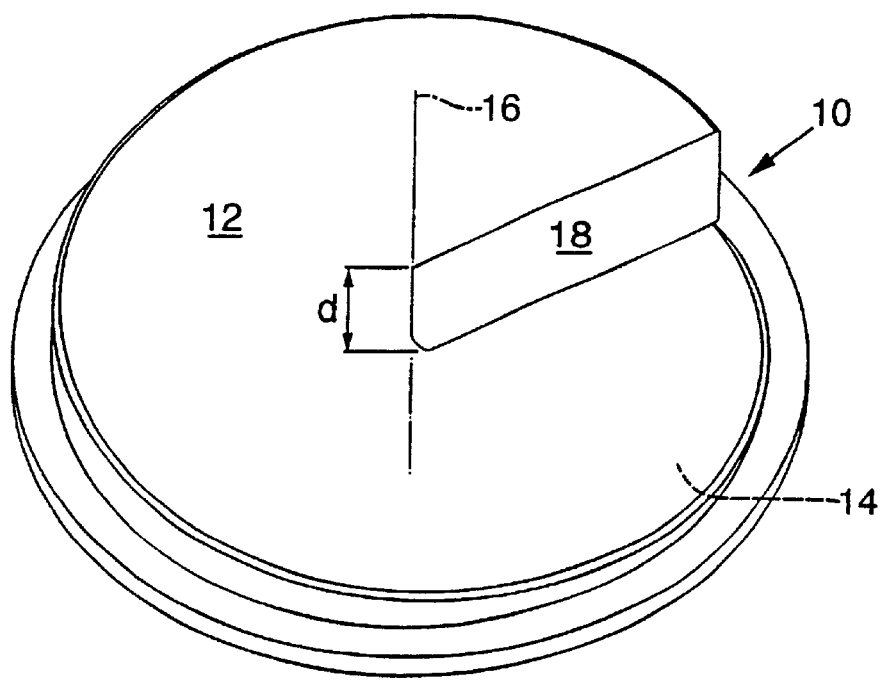
FIG. 1 shows a phase plate for use in a radiation receiving apparatus.

FIG. 1 shows a phase plate 10 in the form of a disc having an upper surface 12 and a lower planar surface 14. The surfaces 12 and 14 comprise an aperture for the passage of radiation. Radiation transmitted by the apparatus passes firstly through the lower surface 14, passes through the body of the plate 10 and then emerges through the upper surface 12. Radiation received by the apparatus travels in an opposite direction. The plate 10 has a central axis 16 extending normal to, and through the centre of, the lower surface 14 and through the centre of the upper surface 12.

The upper surface 12 is provided with a helical and step profile which is defined by a radius of the disc which is perpendicular to the central axis 16, gradually and uniformly moving a distance d along the central axis as it sweeps through 360° about the central axis 16. This results in a step 18 being provided in the upper surface 12. In angular terms a radius locates, at the step has a location of 0° and 360°. The disc has a constant thickness along any radius of the disc at a particular angular position. However, this constant thickness uniformly decreases as the radius sweeps from 0° to 360°.

Before describing the radiation receiving apparatus, the effect of the phase plate on a beam of circularly polarised radiation passing through it will be described. In this embodiment the plate is made of a birefringent material, for example sapphire. Assuming that the beam has a uniform Gaussian profile and it travels so that its peak of intensity parallel to, and coincident with, the central axis 16, then on emerging from the lower surface 14, parts of the beam located on a circular path centred on the central axis 16 will have passed through different thicknesses of material. Since the beam is circularly polarised, it can be resolved into two equal components of electric field $E_H$ (horizontal) and $E_V$ (vertical) at any arbitrary angle which are 90° out of phase. The thickness of the plate is chosen so that between its greatest thickness (that is at an angular location of 0°) and its least thickness (that is at an angular location of 360°) the horizontal and vertical components of a circularly polarised beam passing through will suffer a differential phase delay of one wavelength. The differential phase delays are caused by the birefringent of the plate material. The electrical field component which encounters a high refractive index will travel slowly through the plate and the perpendicular electric field component which encounters a low refractive index will travel quickly through the plate. As a consequence of this, the differential phase delay induced by the phase plate at point about the central axis 16 will vary as follows:

| Angular Location | Differential Phase Delay |
| --- | --- |
| 0° | 0 |
| 90° | $\lambda/4$ |
| 180° | $\lambda/2$ |
| 270° | $3\lambda/4$ |
| 360° | $\lambda$ or 0 |

Figure 2:
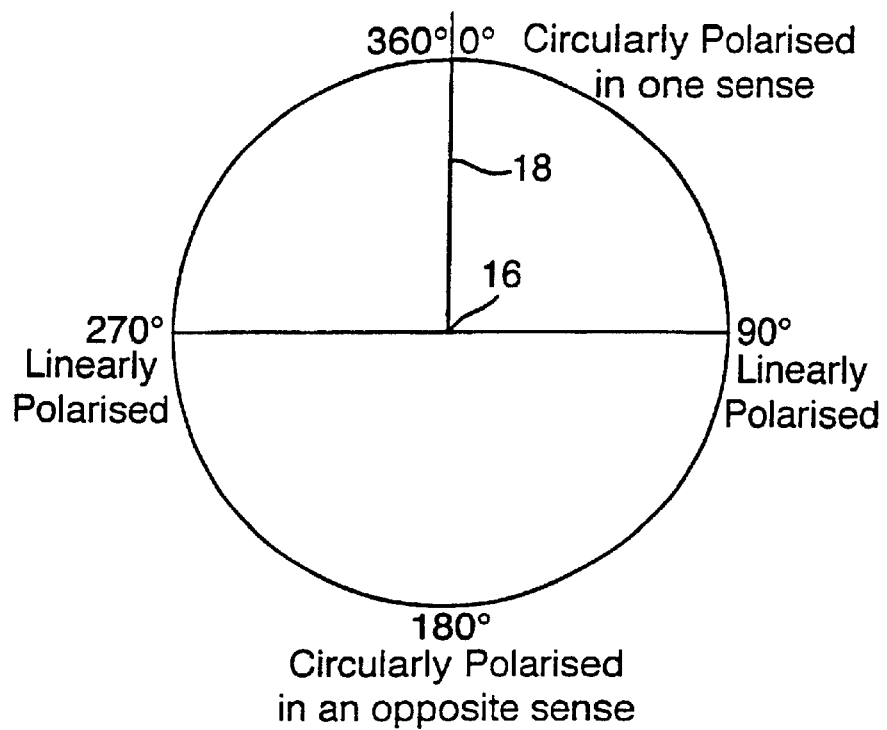
FIG. 2 shows a plan view of the phase plate of FIG. 1 and variation in polarisation about it.

This angular variation in differential phase delay causes an angular variation in polarisation state of the beam about the central axis as is shown in FIG. 2.

An alternative embodiment of a phase plate is shown in FIG. 3, denoted by the numeral 20. Rather than being made out of birefringent material, it has a shape which provides such properties. The phase plate 20 has a similar helical and step profile. However, the phase plate has machined into it a series of parallel slots 22 so that the shape of the phase plate is provided by a series of parallel fins 24 having variations in height so as to provide the profile. For convenience the fins are integral with, and supported by, a base 26. The thickness of the fins and their separation is arranged to be much less than the wavelength of radiation to be received. The fins cause a differential phase delay in the $E_H$ and $E_V$ components of the circularly polarised radiation. The component perpendicular to the fins travels more rapidly than the component which is parallel to the fins. Since the purpose of the fins is simply to provide a thickness of material for the radiation to pass through which varies as a function of angle, it should be understood that the fins could be provided having equal and uniform heights and the depths of the slots varied to provide the angular variation of thickness. However, it is easier to make a phase plate having a variation in fin height rather than slot depth.

Having now explained how the phase delay plate works, operation of a radiation receiving antenna system 1 incorporating such a phase plate can be readily explained. It is shown schematically in FIG. 4 and denoted by the numeral 30. It comprises a reflector 32, a phase plate 34, a lens 36, a microwave horn 38, an ortho mode transducer (OMT) 40 and a phase detector 42. The apparatus is configured to receive (and in certain embodiments transmit) circularly polarised microwave radiation. In certain circumstances, it is desirable to know the direction from which the radiation comes. Since the reflector 32 is in the shape of a cone having a central axis and apex pointing towards the horn 38, the system acts as an omnidirectional antenna in which radiation comes from all directions in an azimuthal plane which is received by the system, will be reflected by the reflector 32 and pass through the phase plate 34. The effect that the phase plate will have on the radiation depends on the angular location at which the radiation passes through the plate. The variation of effect with angular location has been described above in relation to FIG. 2. Of course, in the embodiment shown in FIG. 3, the angular location of the phase plate which the radiation passes through is dependent on the direction of the radiation. Therefore, the direction of the radiation governs the effect applied to the radiation.

On leaving the phase plate 34, the radiation needs to be collected and have the phase relationship between the components $E_H$ and $E_V$ measured in order to determine the direction from which the radiation has come. To provide for efficient collection the lens 26 is provided. Of course a lens is not necessary for a very large horn which has an aperture about the same size as the phase plate. The radiation passes through and is focussed by the lens 26 and is collected by the microwave horn 38. The horn 38 feeds the radiation to the OMT 40 which is an arrangement to split the radiation into its components $E_H$ and $E_V$.

In one embodiment the OMT 40 comprises a body 44 having an input 46 and two output arms 47 and 48. The body also has an adjustable (or pre-set) end stop 49. The configuration of the alms and the end stop is arranged so that component $E_H$ is output through one arm and component $E_V$ is output through the other. In an alternative embodiment, after passing through the phase plate and suitable focussing means, the radiation is incident en a wire grid arranged to reflect one of the components to one side and to permit the other of the components to pass straight through. Each of the components can then be collected by a microwave horn. This embodiment is bulkier than the one described above and requires the use of two horns rather than a single horn.

The separated components are fed to the phase detector 42. Once their phases have been measured, the direction of the radiation can be determined.

Although the apparatus has been described receiving radiation, in certain embodiments it is preferred for it both to transmit and receive. For example, in a communications system, if a unit or station receives a signal to which it is convenient or is necessary to respond, such as an interrogation signal, it is desirable to determine the direction from which the signal originates. In this way a response signal can be transmitted in that direction only, rather than omnidirectionally.

It should be noted that the cone shaped reflector 32 will reflect some received radiation through the centre of the phase plate. This is generally undesirable since in this region there is not such a clear angular variation. Radiation from a particular direction which falls on either side of the centre will undergo significantly different differential phase shifts. Therefore it is preferred to truncate the cone by removing its pointed end to ensure that no reflection into the phase plate occurs from this part of the reflector. In this way received radiation will be reflected largely through the periphery of the phase plate where the differential phase change will be least ambiguous. However, once the radiation has passed through the phase plate it is convenient for it to be more concentrated since this reduces the size of the system 30. Therefore the truncated pointed end is located between the phase plate 34 and the lens 26 with its apex pointing towards the horn 38 and surrounded by a ring reflector in the shape of a tapering sleeve. The taper angles of the pointed end and the tapering sleeve are equal (typically 45°) and so a uniform gap is provided between them. The tapering sleeve collects radiation which emerges from the phase plate and reflects it towards the pointed end. On striking the pointed end, the radiation is reflected towards the horn where it is collected. The arrangement concentrates the radiation, allowing more compact system elements and spacing of such elements. Since certain of the elements are small, others of the elements, for example the lift phase plate, can be made relatively bigger. As the size of the phase plate is increased relative to the radiation footprint, the angular position of the phase plate through which the radiation has passed becomes less ambiguous.

Systems using directional communications channels typically use circularly polarised radiation. However, the phase plate naturally induces an angularly dependent polarisation change to radiation which passes through it and so the system has to be arranged such that the polarisation state of the transmitted radiation is not changed. In certain embodiments of the system transmitted radiation is introduced at a point from which it does not have to travel through the phase plate. This could conveniently be between the phase plate 34 and the reflector 32. In one embodiment this is achieved by locating a miniature co-axial cable on the phase plate and locating a small horn at the centre of the face of the phase plate facing the reflector 32. In another embodiment the radiation is launched into the phase plate from one side so that the radiation travels towards the centre of the phase plate between the highest fins so as to be confined between them. A 45° reflector suitably located transmits the radiation out of the phase plate towards the reflector 32. Metal coating of the fins may help to confine the radiation.

Figure 5:
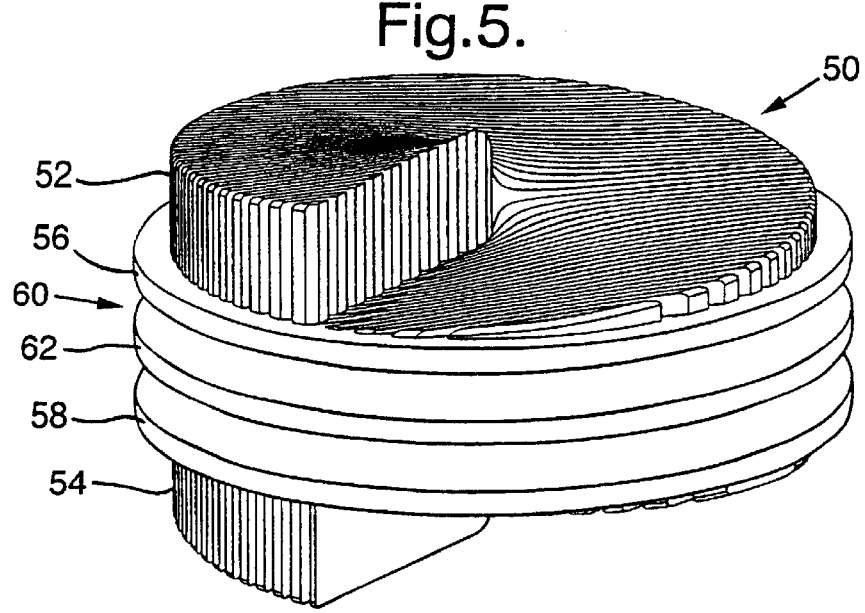
FIG. 5 shows an arrangement of a pair of phase plates.

An arrangement 50 of a pair of phase plates which does not change the polarisation state of transmitted radiation passing through it is shown in FIG. 5. The arrangement 50 has a pair of fin structures 52 and 54, each similar to that described in FIG. 3. The structures are supported by, and integral with, respective bases 56 and 58. In the arrangement 50 the bases 56 and 58 are placed adjacent to each other with a gap 60 between them. The structures 52 and 54 are orientated such that their steps coincide at the same angular location. The structures differ in that in the structure 52 the fins are parallel to the step and in structure 54 the fins and the step are angularly offset by 45°. Of course, the particular orientations of the steps relative to the fins may be other than described. What is important is for the fins on each plate to be at 45° to each other and for the thickness of structure on either side of the gap at corresponding locations to be substantially the same. A Faraday rotator plate 62 is located in the gap 60. The plate 62 induces a rotation in polarisation of 45° in radiation passing through it. When the arrangement 50 is receiving radiation the plate 62 rotates the polarisation of the radiation such that no discontinuity is encountered. In other words, a component of the radiation having its polarisation parallel to the fins of the structure 52, has its polarisation rotated by 45° such that its polarisation is now parallel to the fins of the structure 54. When the arrangement is transmitting radiation a first component of the radiation having its polarisation parallel to the fins of the structure 54 has its polarisation rotated by 45° such that, on entering the structure 52 which is at 45° to the structure 54, its polarisation is perpendicular to the fins of structure 52. Equally, a second component, perpendicular to the first component:, travels through the structure 54 with its polarisation perpendicular to the fins and through the structure 52 with its polarisation parallel to the fins. In other words, each of the perpendicular components travels through two equal thicknesses, one of which is parallel and one of which is perpendicular to the polarisation of the component. As a consequence of this, the arrangement 50 induces equal phase delays in each of the components but no relative phase delay. This applies because the plate 62 is a non-reciprocal device which produces the same effect regardless of the direction of radiation passing through it.

In the arrangement it is convenient for each structure 52 and 54 to induce a maximum relative phase delay of 180° between the components so that received radiation passing through suffers a maximum relative phase delay of 360°.

Figure 6:
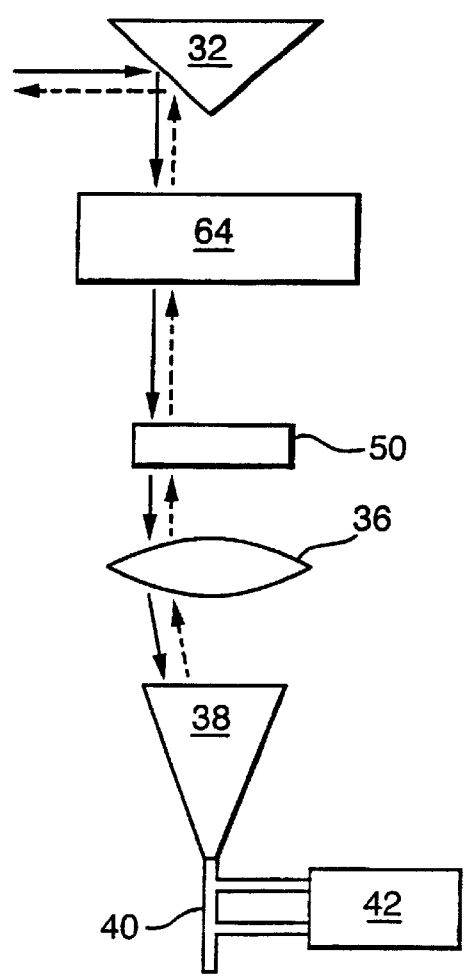
FIG. 6 shows a transceiver.

A transceiver incorporating the arrangement 50 is shown in FIG. 6. The transceiver has a number of similarities to the apparatus of FIG. 4 and, in receiving microwave radiation, it operates in an identical fashion. As has been discussed above, the arrangement 50 produces the same effect on received circularly polarised radiation as the phase plates shown in, and described in relation to FIGS. 1 and 3.

The transceiver has a beam steering device 64 which is described in copending application GB [filed on the same day as this application]. The device 64 is electronically steerable. When the transceiver is operating in a receive mode it is passive and the device 64 does not operate. The direction of incident radiation is determined and then the device 64 energises so as to direct a signal, such as a response signal, in the appropriate direction.

Figure 7:
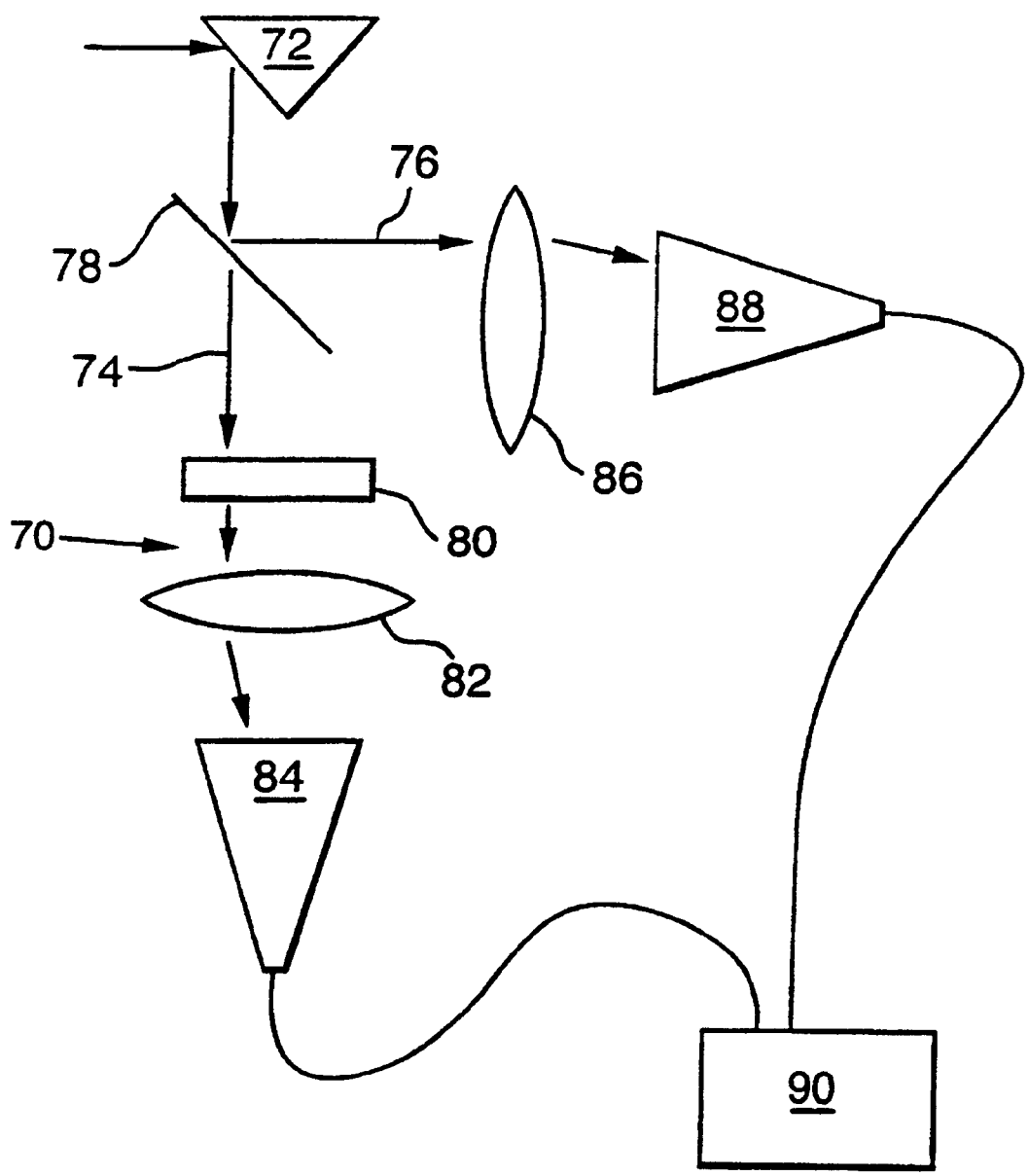
FIG. 7 shows another radiation receiving apparatus.

Another embodiment of a receiving apparatus is shown in FIG. 7. The apparatus is denoted by numeral 70. In common with the apparatus 30, the apparatus 70 has a conical reflector 72 which reflects radiation from an azimuthal plane towards some form of energy collector, for example a microwave horn arrangement. Reflected radiation passes through a suitable means to split the radiation into its components $E_V$ and $E_H$ 74 and 76, for example, a wire grid 78. One component, for example $E_V$ 74, passes through a phase plate 80 having a helical/step profile and is focussed by a lens 82 into a horn 84. Unlike the other phase plates shown in, and described in relation to, FIGS. 1, 3 and 5, the phase plate 80 is isotropic and does not have any birefringent properties. As a result it simply induces an angularly dependent phase delay in the component $E_V$ 74. The other component, for example $E_H$ 76, does not undergo any phase change at all and is focussed by a lens 86 into a horn 88 in order to be used as a reference signal against the phased delayed signal. The relative phase delay between the components $E_V$ and $E_H$ is detected in a phase detector 90 and is used to determine the part of the phase plate 80 through which the radiation has passed and thus its direction.

Although the invention has been described determining the direction of circularly polarised radiation this is simply one example of radiation which has a predetermined polarisation state. Since the way in which the differential phase delay varies about the phase plate is known, then the direction of radiation in any polarisation state can be determined so long as its original polarisation state was known.

In another embodiment, the phase plates of FIGS. 1, 3 and 5 are replaced by a plate which has an angular variation in the degree to which it rotates the polarisation state of radiation passing through it rather than the degree to which it induces a differential phase delay. This would be achieved by having an angular variation in the degree to which differential relative attenuation of the magnitudes of the components of electric field $E_H$ and $E_V$ occurs. Such a plate, assuming it to be nominally circular, may induce a rotation in linearly polarised radiation of 0° at an angular position of 0° and a rotation of 360° at an angular position of 360°. Of course, it may simply be that a differential rotation of 0° to 360° occurs at angular positions from 0° to 360°.

The examples shown have been described operating with radiation travelling in free space. Alternatively the radiation could be collected and transmitted as energy in waveguides with appropriate operations being performed on it to produce the direction finding effect of the invention.

What is claimed is:

1. A system for receiving radiation comprising polarisation varying means to induce an angularly dependent variation in polarisation state and detection means to measure the polarisation state of the radiation to determine the direction from which it originates.

2. A system according to claim 1 characterised in that the polarisation varying means produces a relative change between at least two components of the radiation.

3. A system according to claim 2 characterised in that the two components pass through the polarisation varying means.

4. A system according to claim 2 characterised in that one component passes through the polarisation varying means and the other component serves as a reference.

5. A system according to claim 2 characterised in that the polarisation varying means produces a differential phase delay between the two components.

6. A system according to claim 2 characterised in that the polarisation varying means converts linearly polarised radiation into circularly polarised radiation.

7. A system according to claim 2 characterised in that the polarisation varying means converts circularly polarised radiation into linearly polarised radiation.

8. A system according to claim 2 characterised in that the polarisation varying means produces a change in the relative magnitudes of the two components.

9. A system according to claim 2 characterised in that the polarisation varying means rotates the polarisation state of the radiation.

10. A system according to claim 9 characterised in that the polarisation varying means rotates the polarisation state of linearly polarised radiation.

11. A system according to claim 2 characterised in that the polarisation varying means comprises a phase plate which induces a variable phase delay dependent on the angular position at which the radiation passes through the plate.

12. A system according to claim 11 characterised in that the phase delay is induced by the phase plate having a physical thickness which varies angularly about the phase plate.

13. A system according to claim 2 characterised in that the polarisation varying means has birefringent properties which cause the components to propagate differently through the plate.

14. A system according to claim 2 characterised in that components propagates through the polarisation varying means at different speeds.

15. A system according to claim 2 comprising a splitter which splits the radiation into the two components.

16. A system according to claim 15 characterised in that the split occurs before the radiation has had induced in it a variation in polarisation state.

17. A system according to claim 15 characterised in th at the split occurs after the radiation has had induced in it a variation in polarisation state.

18. A system according to claim 1 comprising a radiation collector.

19. A system according to claim 1 which receives microwave radiation.

20. A system according to claim 1 which receives millimetric radiation.

21. A system according to claim 1 which receives radiation in the Ka band (26.5 to 40 GHz).

22. A system according to claim 1 which is a receiver in a communications system.

23. A system according to claim 1 which is a transmitter and receiver unit.

24. A communications system comprising a radiation receiving system in accordance with claim 1.

25. A method of determining the direction from which radiation originates comprising the steps of inducing a variation in polarisation state of the radiation the variation being angularly dependent and measuring the polarisation state.

* * * * *